US008663916B2

(12) United States Patent
Qiu (10) Patent No.: US 8,663,916 B2
(45) Date of Patent: Mar. 4, 2014

(54) METHODS FOR PRODUCING ANTIFUNGAL BIFUNCTIONAL MOLECULES FOR TREATING FUNGAL INFECTION (75) Inventor: Xiao-Qing Qiu, Sichuan (CN)

(73) Assignee: Pheromonicin Biotech, Ltd., Road Town (VG)

( * ) Notice: Subject to any disclaimer, the term of this patent is extended or adjusted under 35 U.S.C. 154(b) by 131 days.

(21) Appl. No.: 13/048,776

(22) Filed: Mar. 15, 2011

(65) Prior Publication Data

US 2012/0088270 A1 Apr. 12, 2012

Related U.S. Application Data (62) Division of application No. 11/338,117, filed on Jan. 23, 2006, now Pat. No. 7,915,382.

(51) Int. Cl.
*C12Q 1/68* (2006.01)
(52) U.S. Cl.
USPC ............ 435/6; 435/69.1; 435/7.1; 435/320.1; 435/252
(58) Field of Classification Search
None
See application file for complete search history.

(56) References Cited

U.S. PATENT DOCUMENTS 6,942,993 B2  9/2005 Qiu
7,915,382 B2 * 3/2011 Qiu ................................ 530/350
8,367,066 B2 * 2/2013 Qiu ............................ 424/183.1
2003/0078207 A1  4/2003 Qiu
2003/0113293 A1  6/2003 Bermudes et al.

OTHER PUBLICATIONS

Mankovich et al., DNA and Amino Acid Sequence Analysis of Structural and Immunity Genes of Colicins Ia and Ib, Journal of Bacteriology, 1986, pp. 228-236, vol. 168.
Notice of Allowance dated Nov. 16, 2010 as received in related U.S. Appl. No. 11/338,117.
Office Action dated Jul. 13, 2010 as received in related U.S. Appl. No. 11/338,117.
Office Action dated Nov. 24, 2009 as received in related U.S. Appl. No. 11/338,117.
Office Action dated Aug. 23, 2007 as received in related U.S. Appl. No. 11/338,117.
Restriction Requirement dated Feb. 13, 2007 as received in related U.S. Appl. No. 11/338,117.
U.S. Appl. No. 13/048,772 filed Mar. 15, 2011.
U.S. Appl. No. 13/048,777 filed Mar. 15, 2011.

* cited by examiner

*Primary Examiner* — Hope Robinson
(74) *Attorney, Agent, or Firm* — Maschoff Brennan (57) ABSTRACT

The present invention is directed to methods of using nucleic acid molecules encoding for fusion peptides to produce the fusion peptides. The methods can include preparing or providing the nucleic acid molecules that having a fungal targeting agent (e.g., a fungal pheromone, such as alpha-mating pheromone) and a channel-forming domain consisting essentially of amino acids 451-626 of colicin Ia. The nucleic acid molecules can be transfected into host cells to produce the fusion peptide. The fusion peptides of the peptides of the present invention are particularly useful for the treatment of fungal infections in a wide variety of organisms.

19 Claims, 9 Drawing Sheets

SEQUENCE LISTING

<160> NUMBER OF SEQ ID NOS: 8

<210> SEQ ID NO 1
<211> LENGTH: 528
<212> TYPE: DNA
<213> ORGANISM: Escherichia coli
<220> FEATURE:
<221> NAME/KEY: misc_feature
<222> LOCATION: (1)..(528)
<223> OTHER INFORMATION: Gene of colicin Ia

<400> SEQUENCE: 1

```
gacgcaatta atttcacaac agagttcctg aaatcagttt cagaaaaata tggtgcaaaa      60
gctgagcagt tagccagaga gatggccggg caggctaaag ggaagaaaat acgtaatgtt     120
gaagaggcat taaaaacgta tgaaaagtac cgggctgaca ttaacaaaaa aattaatgca     180
```

| | |
|---|---|
| aaagatcgtg cagcgattgc cgcagccctt gagtctgtga agctgtctga tatatcgtct | 240 |
| aatctgaaca gattcagtcg gggactggga tatgcaggaa aatttacaag tcttgctgac | 300 |
| tggatcactg agtttggtaa ggctgtccgg acagagaact ggcgtcctct ttttgttaaa | 360 |
| acagaaacca tcatagcagg caatgccgca acggctcttg tggcactggt cttcagtatt | 420 |
| cttaccggaa gcgctttagg cattatcggg tatggtttac tgatggctgt caccggtgcg | 480 |
| ctgattgatg aatcgcttgt ggaaaaagcg aataagttct ggggtatt | 528 |

<210> SEQ ID NO 2
<211> LENGTH: 42
<212> TYPE: DNA
<213> ORGANISM: Artificial Sequence
<220> FEATURE:
<223> OTHER INFORMATION: Oligonucleotide encoding Candida albicans
      a-mating pheromone

<400> SEQUENCE: 2

| | |
|---|---|
| gggtttcgtc tcacaaactt cggatacttt gagcccggca aa | 42 |

<210> SEQ ID NO 3
<211> LENGTH: 14
<212> TYPE: PRT
<213> ORGANISM: Artificial Sequence
<220> FEATURE:
<223> OTHER INFORMATION: Amino acid sequence of Candida albicans
      a-mating pheromone

<400> SEQUENCE: 3

Gly Phe Arg Leu Tyr Asn Phe Gly Tyr Phe Glu Pro Gly Lys
1               5                   10

<210> SEQ ID NO 4
<211> LENGTH: 570
<212> TYPE: DNA
<213> ORGANISM: Artificial Sequence
<220> FEATURE:
<223> OTHER INFORMATION: Gene encoding Ph-CA1

<400> SEQUENCE: 4

| | |
|---|---|
| gacgcaatta atttcacaac agagttcctg aaatcagttt cagaaaaata tggtgcaaaa | 60 |
| gctgagcagt tagccagaga gatggccggg caggctaaag ggaagaaaat acgtaatgtt | 120 |
| gaagaggcat taaaaacgta tgaaaagtac cgggctgaca ttaacaaaaa aattaatgca | 180 |
| aaagatcgtg cagcgattgc cgcagccctt gagtctgtga agctgtctga tatatcgtct | 240 |
| aatctgaaca gattcagtcg gggactggga tatgcaggaa aatttacaag tcttgctgac | 300 |
| tggatcactg agtttggtaa ggctgtccgg acagagaact ggcgtcctct ttttgttaaa | 360 |
| acagaaacca tcatagcagg caatgccgca acggctcttg tggcactggt cttcagtatt | 420 |
| cttaccggaa gcgctttagg cattatcggg tatggtttac tgatggctgt caccggtgcg | 480 |
| ctgattgatg aatcgcttgt ggaaaaagcg aataagttct ggggtattgg gtttcgtctc | 540 |
| acaaacttcg gatactttga gcccggcaaa | 570 |

<210> SEQ ID NO 5
<211> LENGTH: 190
<212> TYPE: PRT
<213> ORGANISM: Artificial Sequence
<220> FEATURE:
<223> OTHER INFORMATION: Amino acid sequence of Ph-CA1

<400> SEQUENCE: 5

Asp Ala Ile Asn Phe Thr Thr Glu Phe Leu Lys Ser Val Ser Glu Lys

```
                1               5                  10                 15
Tyr Gly Ala Lys Ala Glu Gln Leu Ala Arg Glu Met Ala Gly Gln Ala
                20                 25                 30

Lys Gly Lys Lys Ile Arg Asn Val Glu Glu Ala Leu Lys Thr Tyr Glu
            35                 40                 45

Lys Tyr Arg Ala Asp Ile Asn Lys Lys Ile Asn Ala Lys Asp Arg Ala
        50                 55                 60

Ala Ile Ala Ala Ala Leu Glu Ser Val Lys Leu Ser Asp Ile Ser Ser
65                 70                 75                 80

Asn Leu Asn Arg Phe Ser Arg Gly Leu Gly Tyr Ala Gly Lys Phe Thr
                85                 90                 95

Ser Leu Ala Asp Trp Ile Thr Glu Phe Gly Lys Ala Val Arg Thr Glu
            100                105                110

Asn Trp Arg Pro Leu Phe Val Lys Thr Glu Thr Ile Ile Ala Gly Asn
        115                120                125

Ala Ala Thr Ala Leu Val Ala Leu Val Phe Ser Ile Leu Thr Gly Ser
    130                135                140

Ala Leu Gly Ile Ile Gly Tyr Gly Leu Leu Met Ala Val Thr Gly Ala
145                150                155                160

Leu Ile Asp Glu Ser Leu Val Glu Lys Ala Asn Lys Phe Trp Gly Ile
                165                170                175

Gly Phe Arg Leu Tyr Asn Phe Gly Tyr Phe Glu Pro Gly Lys
            180                185                190
```

<210> SEQ ID NO 6
<211> LENGTH: 570
<212> TYPE: DNA
<213> ORGANISM: Artificial Sequence
<220> FEATURE:
<223> OTHER INFORMATION: Gene encoding Ph-CA2

<400> SEQUENCE: 6

```
gggtttcgtc tcacaaactt cggatacttt gagcccggca agacgcaat taatttcaca       60
acagagttcc tgaaatcagt ttcagaaaaa tatggtgcaa agctgagca gttagccaga      120
gagatggccg ggcaggctaa agggaagaaa atacgtaatg ttgaagaggc attaaaaacg    180
tatgaaaagt accgggctga cattaacaaa aaaattaatg caaaagatcg tgcagcgatt    240
gccgcagccc ttgagtctgt gaagctgtct gatatatcgt ctaatctgaa cagattcagt    300
cggggactgg gatatgcagg aaaatttaca agtcttgctg actggatcac tgagtttggt    360
aaggctgtcc ggacagagaa ctggcgtcct cttttgtta aaacagaaac catcatagca     420
ggcaatgccg caacggctct tgtggcactg tcttcagta ttcttaccgg aagcgcttta     480
ggcattatcg ggtatggttt actgatggct gtcaccggtg cgctgattga tgaatcgctt    540
gtggaaaaag cgaataagtt ctggggtatt                                      570
```

<210> SEQ ID NO 7
<211> LENGTH: 190
<212> TYPE: PRT
<213> ORGANISM: Artificial Sequence
<220> FEATURE:
<223> OTHER INFORMATION: Amino acid sequence of Ph-CA2

<400> SEQUENCE: 7

```
Gly Phe Arg Leu Tyr Asn Phe Gly Tyr Phe Glu Pro Gly Lys Asp Ala
1               5                  10                 15

Ile Asn Phe Thr Thr Glu Phe Leu Lys Ser Val Ser Glu Lys Tyr Gly
            20                 25                 30
```

```
Ala Lys Ala Glu Gln Leu Ala Arg Glu Met Ala Gly Gln Ala Lys Gly
            35                  40                  45

Lys Lys Ile Arg Asn Val Glu Glu Ala Leu Lys Thr Tyr Glu Lys Tyr
 50                  55                  60

Arg Ala Asp Ile Asn Lys Lys Ile Asn Ala Lys Asp Arg Ala Ala Ile
 65                  70                  75                  80

Ala Ala Ala Leu Glu Ser Val Lys Leu Ser Asp Ile Ser Ser Asn Leu
                 85                  90                  95

Asn Arg Phe Ser Arg Gly Leu Gly Tyr Ala Gly Lys Phe Thr Ser Leu
                100                 105                 110

Ala Asp Trp Ile Thr Glu Phe Gly Lys Ala Val Arg Thr Glu Asn Trp
            115                 120                 125

Arg Pro Leu Phe Val Lys Thr Glu Thr Ile Ile Ala Gly Asn Ala Ala
        130                 135                 140

Thr Ala Leu Val Ala Leu Val Phe Ser Ile Leu Thr Gly Ser Ala Leu
145                 150                 155                 160

Gly Ile Ile Gly Tyr Gly Leu Leu Met Ala Val Thr Gly Ala Leu Ile
                165                 170                 175

Asp Glu Ser Leu Val Glu Lys Ala Asn Lys Phe Trp Gly Ile
            180                 185                 190

<210> SEQ ID NO 8
<211> LENGTH: 176
<212> TYPE: PRT
<213> ORGANISM: Escherichia coli

<400> SEQUENCE: 8

Asp Ala Ile Asn Phe Thr Thr Glu Phe Leu Lys Ser Val Ser Glu Lys
 1               5                  10                  15

Tyr Gly Ala Lys Ala Glu Gln Leu Ala Arg Glu Met Ala Gly Gln Ala
             20                  25                  30

Lys Gly Lys Lys Ile Arg Asn Val Glu Glu Ala Leu Lys Thr Tyr Glu
         35                  40                  45

Lys Tyr Arg Ala Asp Ile Asn Lys Lys Ile Asn Ala Lys Asp Arg Ala
     50                  55                  60

Ala Ile Ala Ala Ala Leu Glu Ser Val Lys Leu Ser Asp Ile Ser Ser
 65                  70                  75                  80

Asn Leu Asn Arg Phe Ser Arg Gly Leu Gly Tyr Ala Gly Lys Phe Thr
                 85                  90                  95

Ser Leu Ala Asp Trp Ile Thr Glu Phe Gly Lys Ala Val Arg Thr Glu
            100                 105                 110

Asn Trp Arg Pro Leu Phe Val Lys Thr Glu Thr Ile Ile Ala Gly Asn
        115                 120                 125

Ala Ala Thr Ala Leu Val Ala Leu Val Phe Ser Ile Leu Thr Gly Ser
130                 135                 140

Ala Leu Gly Ile Ile Gly Tyr Gly Leu Leu Met Ala Val Thr Gly Ala
145                 150                 155                 160

Leu Ile Asp Glu Ser Leu Val Glu Lys Ala Asn Lys Phe Trp Gly Ile
                165                 170                 175
```

METHODS FOR PRODUCING ANTIFUNGAL BIFUNCTIONAL MOLECULES FOR TREATING FUNGAL INFECTION

CROSS-REFERENCE TO RELATED APPLICATIONS

This application is a divisional application of U.S. patent application having U.S. Ser. No. 11/338,117, filed in the U.S. on Jan. 23, 2006 and published as Pre-Grant Publication 2006/0264370 now U.S. Pat. No. 7,915,382, which application claims priority under 35 U.S.C. 119(a) to Chinese Patent Application No. 2005100202199, filed on Jan. 21, 2005, which applications are both incorporated herein by specific reference in their entirety.

BACKGROUND

Fungus is opportunistic pathogens in humans. Fungus typically does not infect healthy tissues, yet once tissue defense mechanisms have been compromised, they can readily infect the tissue. One typical model of this opportunistic fungal infection is candidiasis, which is caused by *Candida albicans*.

*Candida albicans* occurs as normal flora in the oral cavity, genitalia, large intestine, and skin of approximately 20% of humans. The risk of infection increases in children and pregnant women; people who use certain antibiotics or have nutritional and organic disease or immunodeficiency (e.g., AIDS) or trauma; and people with invasive devices, e.g., pacemakers. *Candida albicans* and its close relatives account for nearly 80% of nosocomial fungal infections and 30% of deaths from nosocomial infections in general.

Historically, opportunistic, fungal infections in hospitalized patients were rather unusual. Textbooks from the past described these agents as common contaminants with weak pathogenic potential, and infections were considered extreme deviation from the normal. Older ideas concerning these so-called harmless contaminants are now challenged because in those days immunodeficient and debilitated patients had died from their afflictions long before fungal infection took place. However, currently, with the advent of innovative surgeries, drugs, and other therapies that maintain such patients for expected periods, the survival rates of patients have significantly increased and the number of compromised patients has thus increased. One clinical dilemma that cannot be completely eliminated, even with rigorous disinfections, is the exposure of such patients to potential fungal pathogens from even normal flora. Fungal infections in such high-risk patients progress rapidly and are difficult to diagnose and treat. In one study, fungi caused approximately 40% of the deaths from clinically acquired infections. Up to 5% of all nosocomial opportunistic fungi cause infections.

Fungi also present special problems in chemotherapy. A majority of chemotherapeutic drugs used in treating bacterial infection are generally ineffective in combating fungal infection. Moreover, the similarity between fungal and human cells often means drug toxic to fungal cells are capable of harming human cells. A few drugs with special antifungal properties have been developed for treatment of systemic and superficial fungal infections. For example, macrolide polyenes represented by amphotericin B, have a structure that mimics some cell membrane lipids. Amphotericin B which is isolated from a species of streptomycin is by far the most versatile and effective of all antifungal drugs. The azoles are broad-spectrum antifungal drugs with a complex ringed structure. As one of the most effective azole drugs, fluconazole, is used in patients with AIDS-related mycoses.

*Magnaporthe grisea* is the pathogen of a devastating fungal disease of rice plants known as rice blast. The fungus can also cause a similar disease in over 50 grasses, including economically important crops such as barley, wheat, and millet. *Fusarium* is another important genus of fungal pathogens, responsible for devastating diseases such as cereal scab.

SUMMARY

The present invention is directed to novel methods of producing fusion peptides from fusion polynucleotides. The methods can include providing or preparing nucleic acid molecules encoding for peptides that include a fungi specific targeting agent, e.g., a pathogenic fungal peptide pheromone, and a channel-forming colicin or a channel-forming fragment thereof (also referred to herein as "domain"). Peptides comprising a pheromone as the fungi specific targeting agent, and a colicin domain, are referred to herein as "pheromonicin peptides".

The molecular structure of the formed peptides may have the C-terminus of colicin or a channel-forming domain linked with the N-terminus of a fungi specific targeting agent, e.g., a fungal pheromone, or the N-terminus of colicin may be linked with the C-terminus of a fungi specific targeting agent e.g., a fungal pheromone. The fungal pheromone can be from a pathogenic fungus, e.g., *Candidas*. The molecular weight of the peptide may vary, e.g., from about 26,000 to about 70,000 daltons.

The nucleic acid molecules of the present invention may be formed by a variety of methods. One method of forming a peptide of the present invention is by inserting a nucleic acid molecule encoding a fungal pheromone into a selected position of a nucleic acid molecule encoding a colicin, or a channel forming domain thereof, then transfecting the mutant plasmid into a host cell, e.g., *E. coli*, to produce the peptide.

In one embodiment, the peptides encoded by the nucleic acid molecules of the present invention are useful in treating infections of *Candidas* or *Aspergillus* or *Magnaporthes* or *Fusarium*. Exemplary infections are those created by *Candida albicans, Candida tropicalis, Candida parapsilokis, Candida krusei, Candida dubliniensis, Cryptococcus neoformans, A. fumigatus, A. flavus, A. niger, Magnaporthe grisea* and *Fusarium moniforme*.

The invention further provides vectors having the nucleic acid molecules that encode the peptides of the invention. The invention also provides cells, e.g., host cells, comprising the vectors of the invention.

Host cells, including bacterial cells such as *E. coli*, insect cells, yeast or mammalian cells (such as Chinese hamster ovary cells (CHO) or COS cells), can be used to produce the peptides of the invention. Other suitable host cells are known to those skilled in the art. The invention thus provides methods for producing the peptides of the invention comprising the steps of culturing the host cells of the invention and isolating the peptides of the invention therefrom.

In another embodiment, the invention provides a method for preparing a peptide which inhibits growth of a fungus comprising: (i) inserting a nucleic acid molecule encoding colicin, or a channel forming domain thereof, into a selected position of a nucleic acid molecule encoding a fungal targeting agent, e.g., a pheromone; (ii) transfecting the mutant plasmid into a host cell, e.g., an *E. coli* cell; and (iii) allowing said host cell to produce said peptide. In further embodiments, the peptide may be purified from the cells.

In another embodiment, the invention provides a method for preparing a fusion peptide comprising: (i) incorporating a nucleic acid molecule encoding the peptide chain of colicin Ia with a nucleic acid molecule encoding a fungal pheromone such as *Candida albicans* alpha-mating pheromone; and (ii) introducing said nucleic acid molecule encoding the peptide chain of colicin Ia incorporated with said fungal pheromone a following the C-terminus of the colicin Ia to form a nucleic acid molecule that encodes a 639 residue peptide.

In another embodiment, the invention provides a method for preparing a fusion peptide comprising: (i) incorporating a nucleic acid molecule encoding a peptide chain of colicin Ia with a nucleic acid molecule encoding a fungal pheromone such as *Candida albicans* alpha-mating pheromone; and (ii) introducing said nucleic acid molecule before the N-terminus of said colicin Ia to form a nucleic acid molecule that encodes a 639 residue peptide.

In one embodiment, the invention provides a method of treating a subject having a fungal infection comprising: administering to a subject a therapeutically effective amount of a fusion peptide of the present invention, e.g., a peptide comprising a colicin Ia with a fungal targeting agent, e.g., a pheromone. Said subject may have a *Candidas* or *Aspergillus* or *Magnaporthe* or *Fusarium* infection. Specifically, *Candidas* or *Aspergillus* or *Magnaporthe* or *Fusarium* may be selected from the group consisting of *Candida albicans, Candida tropicalis, Candida parapsilokis, Candida krusei, Candida dubliniensis, Cryptococcus neoformans, A. fumigatus, A. flavus, A. niger, Magnaporthe grisea* and *Fusarium moniforme*. The peptides of the instant invention can also be used to treat clinical fugal infections and other fungal infections in crops.

The peptides of the invention can be incorporated into pharmaceutical compositions suitable for administration to a subject. In a preferred embodiment, the pharmaceutical composition comprises a peptide of the invention comprising the *C. albicans* alpha-pheromone and a pharmaceutically acceptable carrier.

The term, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous or parenteral administration (e.g., by injection). Depending on the route of administration, the active compound may be coated in a material to protect the compound from the action of acids and other natural conditions, which may inactivate the compound.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1 schematically depicts the structure of a recombinant plasmid that contains the gene of colicin Ia with the gene of *Candida albicans* alpha-mating pheromone inserted following the C-terminus of colicin Ia in the plasmid pET-15b to form a plasmid referred to herein as pCHCCA1.

FIG. 2 schematically depicts the structure of a recombinant plasmid that contains the gene of colicin Ia with the gene of *Candida albicans* alpha-mating pheromone inserted following the N-terminus of colicin Ia in the plasmid pET-15b to form the plasmid referred to herein as pCHCCA2.

FIG. 3 depicts a growth inhibition assay wherein ATCC 10231 *C. albicans* cells were grown in M-H solid medium and exposed to (A) borate stock solution as control, (B) 50 ul amphotericin B (1 ug/ml), (C) 50 ul fluconazole (3 ug/ml), (D) 50 ul pheromonicin-SA (Ph-SA)(50 ug/ml), the fusion peptide against *Staphylococcus aureus* and (E) 50 ul pheromonicin-CA1 (Ph-CA1)(50 u/ml), the peptide produced by the pCHCCA1 plasmid.

FIG. 4 depicts the inhibition effects of Ph-CA against the growth of ATCC 10231 *C. albicans* cells in M-H liquid medium. The amount of sedimentary fungal filaments at the bottom of flasks indicated the inhibition effects of treatment agents. (A) Control, (B) fluconazole, (C) amphotericin B, (D) Ph-SA, (E) Ph-CA2 produced by pCHCCA2 plasmid and (F) Ph-CA1.

FIG. 5 depicts the inhibition effects of Ph-CA against the growth of *C. albicans* cells in liquid medium. The amount of spores and filaments of ATCC 10231 *C. albicans* cells indicated the inhibition effects. (A) Control, (B) fluconazole, (C) amphotericin B, (D) Ph-SA, (E) Ph-CA2 (F) Ph-CA1. X400.

FIG. 6 depicts the fluorescent imaging of ATCC 10231 *C. albicans* cells treated by Ph-CA1 and stained with 50 nM FITC/600 nM propidium iodide. (A) Control, cells were stained by FITC as green, (B) cells became red after 24 hrs Ph-CA1 treatment (10 ug/ml). X400.

FIG. 7 depicts a growth inhibition assay wherein Huaxi 30168 *Cryptococcus neoformans* cells were grown in M-H solid medium and exposed to (A) and (B) 100 ul amphotericin B (2 ug and 0.5 ug/ml respectively), (C) and (D) 100 ul Ph-CA1 (50 ug and 25 ug/ml respectively).

FIG. 8 depicts a growth inhibition assay wherein Huaxi 30255 *Aspergillus flavus* cells were grown in PDA solid medium and exposed to (A), (B) and (C) 100 ul tricyclazole (5 mg, 0.5 mg, and 0.05 mg/ml respectively), (D) 100 ul Ph-CA1 (50 ug/ml).

FIG. 9 depicts a growth inhibition assay wherein ACCC 30320 *Magnaporthe grisea* cells were grown in PDA solid medium and exposed to (A) 100 ul amphotericin B (0.5 ug/ml), (B) 100 ul tricyclazole (0.5 mg/ml), (C) and (D) 100 ul Ph-CA1 (25 ug and 50 ug/ml respectively).

FIG. 10 depicts a growth inhibition assay wherein ACCC 30133 *Fusarium moniforme* cells were grown in PDA solid medium and exposed to (A) control, (B) 100 ul amphotericin B (0.5 ug/ml), (C) Ph-CA1 100 ul Ph-CA1 (50 ug/ml) and (D) 100 ul tricyclazole (0.5 mg/ml).

FIG. 11 depicts in vivo activity of Ph-CA1 against systemic candidiasis. The *C. albicans* infected mice were untreated or treated by intraperitoneal amphotericin B or Ph-CA1.

FIG. 12 depicts in vivo activity of Ph-CA1 against systemic candidiasis. The *C. albicans* infected mice were untreated or treated by intravenous amphotericin B or Ph-CA1.

FIG. 13 depicts the microscopic view of visceral organs of mice treated with Ph-CA1 30 days. (A) liver, (B) kidney and (C) spleen stained with hematoxylin and eosin. 100X.

All arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The antifungal peptides of the present invention comprise a fungi specific targeting agent e.g., a fungal pheromone, and one or more channel-forming colicins or channel-forming domains thereof. The molecular structure is generally either the C-terminus of a colicin or channel-forming domain thereof, linked with the N-terminus of the fungal specific targeting agent, or the N-terminus of the colicin or channel forming domain thereof, linked with the C-terminus of a fungal specific targeting agent. Although full-length colicin may be used in the methods and compositions of the invention, in some embodiments, only a channel-forming domain is used. In a preferred embodiment, the colicin channel-forming domain consists essentially of amino acids 451-626 of colicin Ia.

Colicins are protein toxins produced by strains of *E. coli*. They are generally classified into groups corresponding to the outer membrane receptor on sensitive *E. coli* cells to which they bind, with colicins that bind to the BtuB protein, the high affinity receptor for vitamin B 12, being known as the E group. E-type colicins are about 60 kDa proteins that have three functional domains each implicated in one of the three stages of cell killing. The C-terminal domain carries the cytotoxic activity, the central domain carries the receptor-binding activity, and the N-terminal domain mediates translocation of the cytotoxic domain across the outer membrane. Three cytotoxic activities are found amongst E-type colicins: (i) a pore-forming ion channel that depolarizes the inner membrane (colicin E1); (ii) an H—N—H endonuclease activity that degrades chromosomal DNA (colicins E2, E7, E8 and E9); and (iii) ribonuclease activities (colicin E3, E4, E5 and E6). Colicin-producing bacteria are resistant against the action of their own colicin through possession of a small immunity protein that inactivates the cytotoxic domain. After binding to *E. coli* cell surface receptors, E-type colicins are translocated to their site of action by a tol dependent translocation system.

The peptides of the present invention maybe prepared by inserting a nucleic acid molecule encoding a fungal pheromone into the selected position of a nucleic acid molecule encoding a colicin, or a channel forming fragment thereof. The resulting transfected mutant plasmid may then inserted into a host cell, e.g., *E. coli*, to produce the peptide. Colicin Ia has the nucleic acid sequence set forth in SEQ ID NO: 1. *Candida albicans* alpha-mating pheromone has the nucleic acid sequence set forth in SEQ ID NO:2 and the amino acid sequence set forth in SEQ ID NO:3.

The peptides of the invention may be used to treat subjects having a fungal infection, e.g., *Candidas, Cryptococcus, Aspergillus, Magnaporthes* or *Fusariums*. Exemplary fungal infections are oral thrush, oesophageal thrush (Oesophagitis), cutaneous (skin) candidiasis, vaginal yeast infection or candida vaginitis, balanitis, and systemic candidiasis. The peptides of the invention may also be used to treat devastating fungal infections in crops.

EXAMPLES

Example 1

A fusion peptide that has been identified as pheromonicin-CA1(Ph-CA1) was created incorporating a peptide chain of colicin Ia with a *Candida albicans* alpha-mating pheromone, wherein the pheromone was c-terminal to the colicin Ia to produce a polynucleotide having the nucleic acid sequence of SEQ ID NO:4 which encodes a polypeptide having the amino acid sequence of SEQ ID NO:5.

Example 2

A second fusion peptide denominated as pheromonicin-CA2 (Ph-CA2) was created by incorporating a peptide chain of colicin Ia with a *Candida albicans* alpha-mating pheromone, wherein the pheromone is n-terminal to the colicin Ia, to produce a polynucleotide having nucleic acid sequence of SEQ ID NO:6 which encodes a polypeptide having the amino acid sequence of SEQ ID NO:7.

Results

Ph-CA1 had definite antifungal effect on *Candida albicans* (ATCC 10231) in vitro and in vivo. In contrast, Ph-CA2 almost had no effect. One in vitro cell growth inhibition assay was performed with M-H or PDA solid mediums. About 5 ul Cells ($10^8$ CFU/ml) of *Candida albicans* (ATCC 10231), *Cryptococcus neoformans* (Huaxi 30168 strain, clinical isolated strain by West China Hospital, Sichuan University), *Aspergillus flavus* (Huaxi 30255 strain), *Magnaporthe grisea* (ACCC 30320 strain, Species Conservation Center, Chinese Academy of Agriculture Sciences), or *Fusarium moniforme* (ACCC 30133 strain) were inoculated on the surface of 10 ml M-H or PDA solid mediums contained in disks. Then 50-100 ul amphotericin B (0.5 ug to 2 ug/ml) or fluconazole (3 ug/ml) or tricyclazole (0.05 mg to 5 mg/ml) or Ph-CA1 (25 to 50 ug/ml) either rinsed in a piece of filter paper or contained in a container then being placed on the surface of the medium, and incubated at 35° C. for 2 to 4 days.

Figure 1:
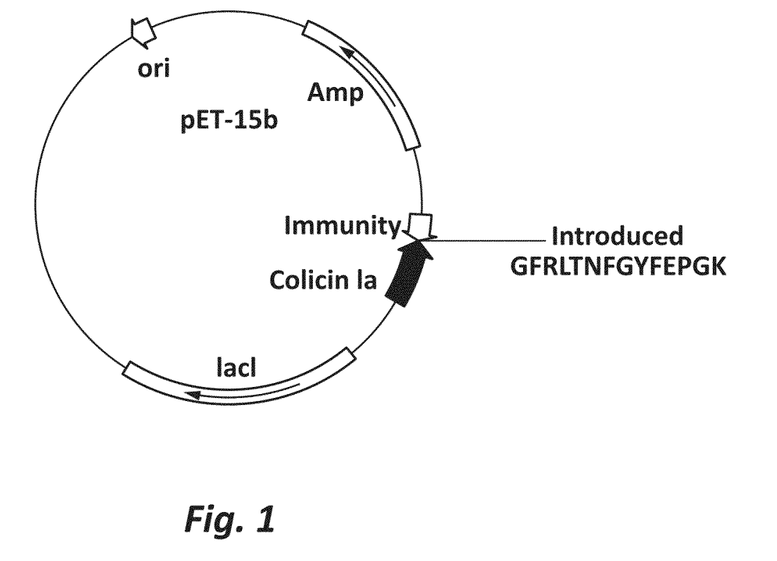
Figure 2:
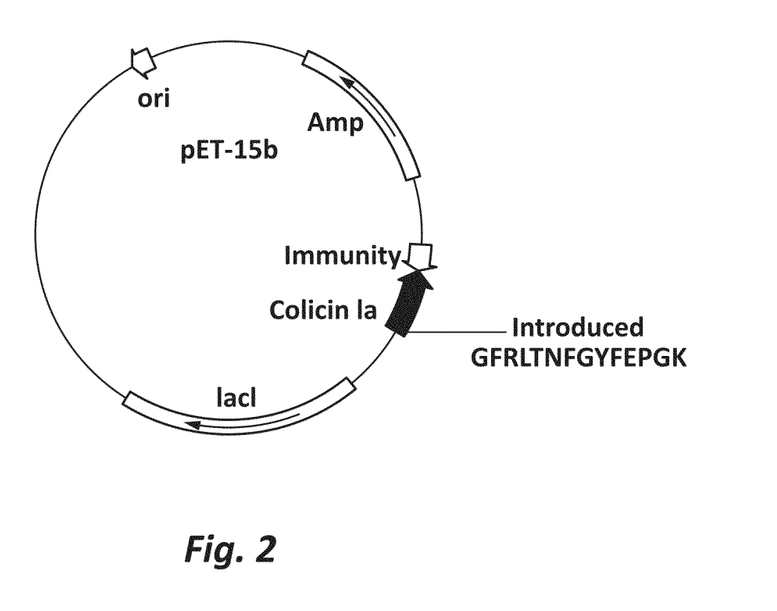
Figure 3:
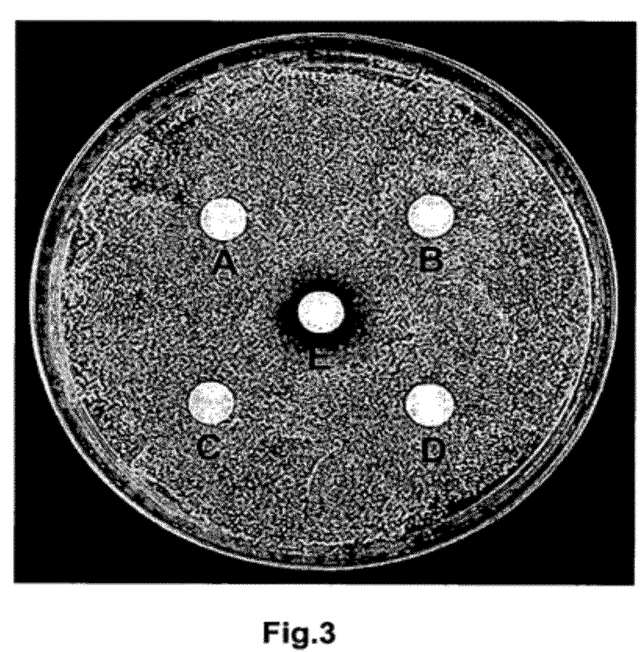

As shown in FIG. 3, only an inhibition-zone surrounds Ph-CA1, while no similar zones were observed with other agents. FIGS. 7 to 10 show that Ph-CA1 had definite antifungal effects against corresponding *Cryptococcus neoformans, Aspergillus flavus, Magnaporthe grisea* and *Fusarium moniforme* cells. On a molar basis, such antifungal effects were one hundred to one thousand times greater than that of known antifungal antibiotics.

In vitro cell growth inhibition assays were performed in 100 ml Klett flasks containing 10 ml of M-H medium which were monitored turbimetrically with a BioRad 550 microplate reader at OD595 nm every 60 min. The filament (mycelium) precipitation at the bottom of flask was counted with a digital photo-recorder every 6 hrs. Cells were inoculated to an initial cell density of about $2.5 \times 10^5$ CFU/ml and shaken at 200 rpm on an orbital shaker at 35° C. Sedimentary fungal filaments appeared in about 36 hrs growing.

Ph-CA1 and Ph-CA2 were added at the start of the culture. The same amount of borate stock solution (50 mM borate, PH9.0), Ph-SA (pheromonicin constructed by colicin Ia and staphylococcal pheromone AgrD1)(10 ug/ml) and several antibiotics preparations (2 ug/ml amphotericin B, 6 ug/ml fluconazole) were used as controls. All assays were expressed in turbidometric absorbance units measured at 595 nm and pictures of the filament sedimentation at the bottom of the flask were taken.

Figure 4:
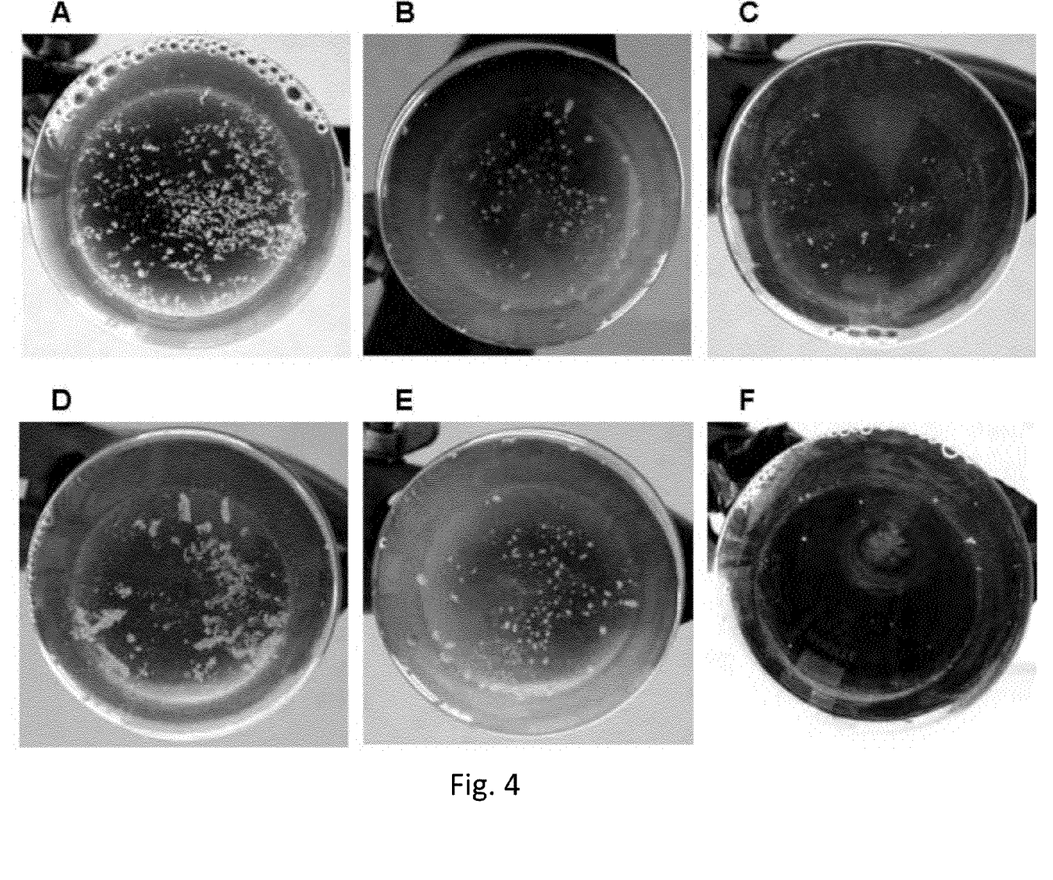
Figure 5:
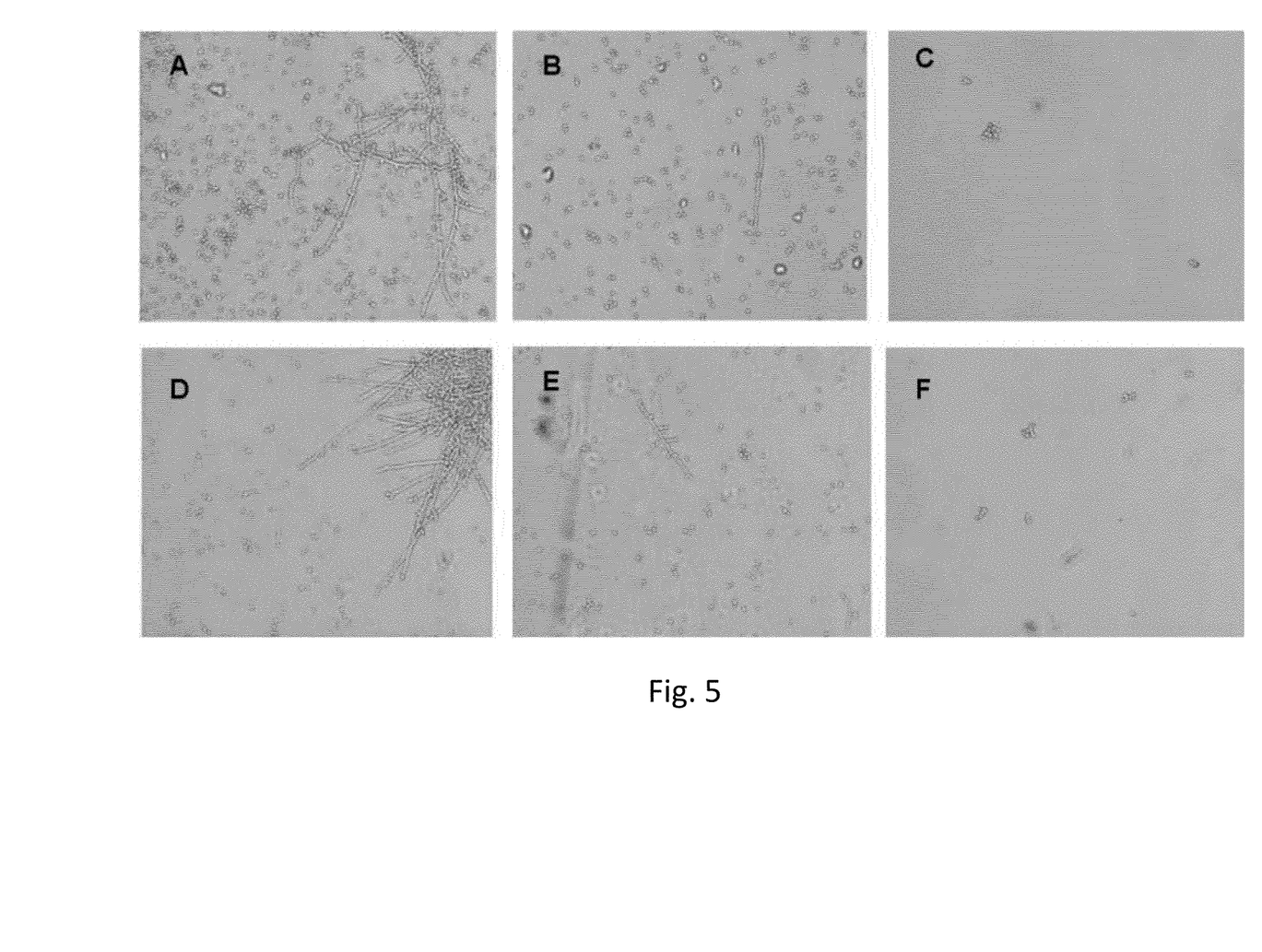

Fluconazole and Ph-SA had no effect on the growth of *C. albicans* compared to untreated controls. In contrast, 10 ug/ml Ph-CA1 completely inhibited *C. albicans* growth, as did 2 ug/ml amphotericin B. 10 ug/ml Ph-CA2 had about 30% of the inhibition effect as the Ph-CA1. Considering the difference in molecular weight between Ph-CA1 (70 kDa) and amphotericin B (about 0.9 kDa), the inhibitory effect of Ph-CA1 against *C. albicans* was approximately ten times greater, on a molar basis, than that of amphotericin B (see FIG. 4). The spores and filaments of 2 ul treated medium were dripped on a slide and observed under microscope. In comparison with control and other treatments, spores were scarcely observed in the amphotericin B and Ph-CA1 (see FIG. 5).

Figure 6:
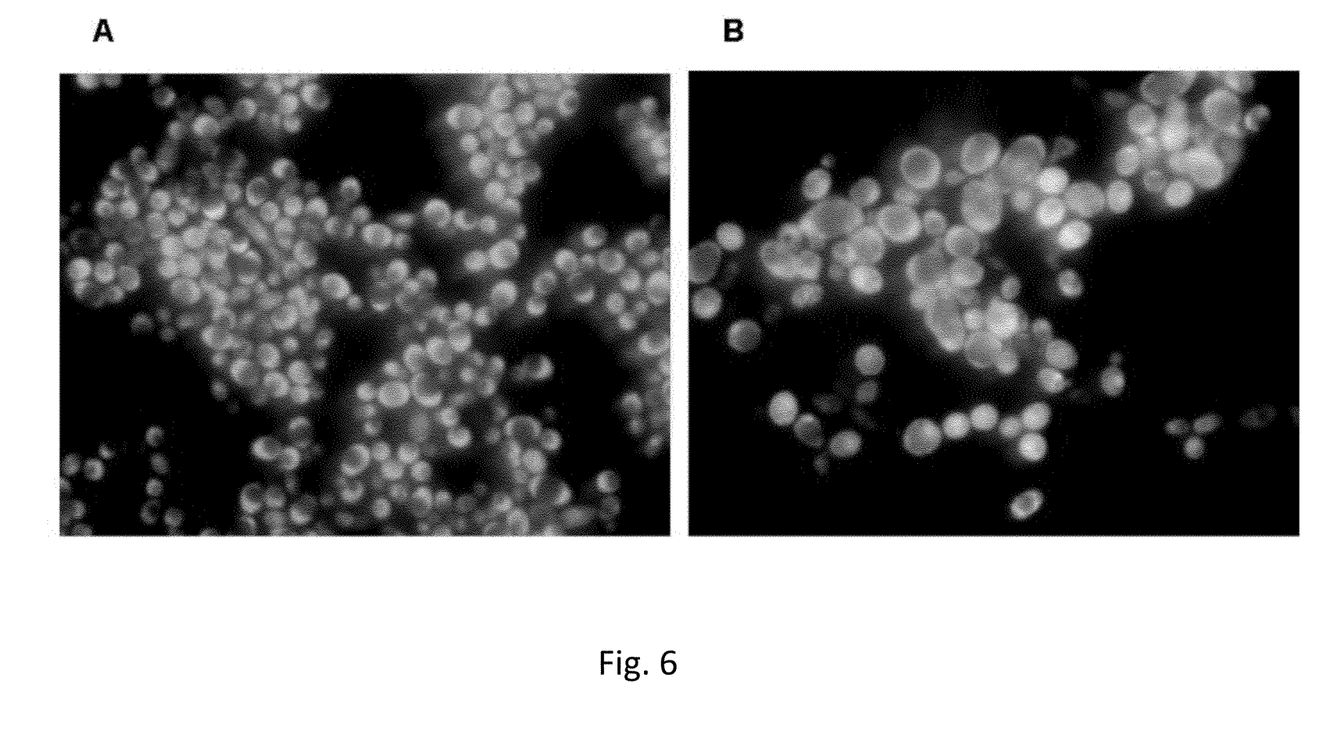
Figure 7:
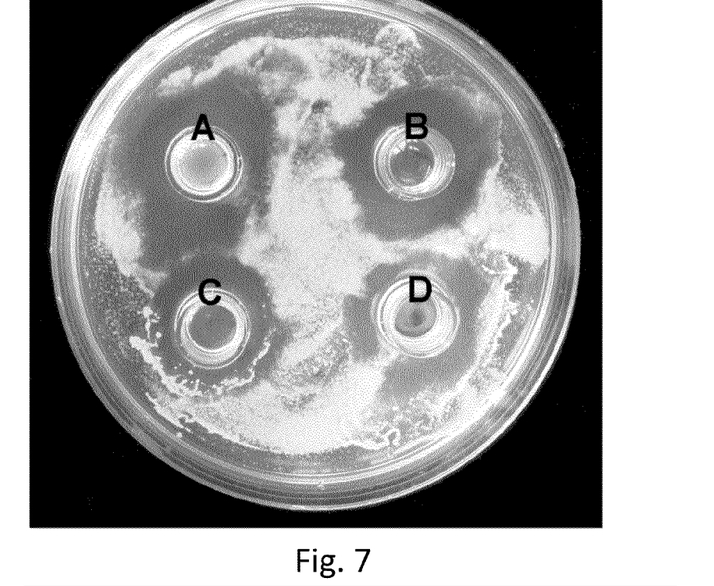
Figure 8:
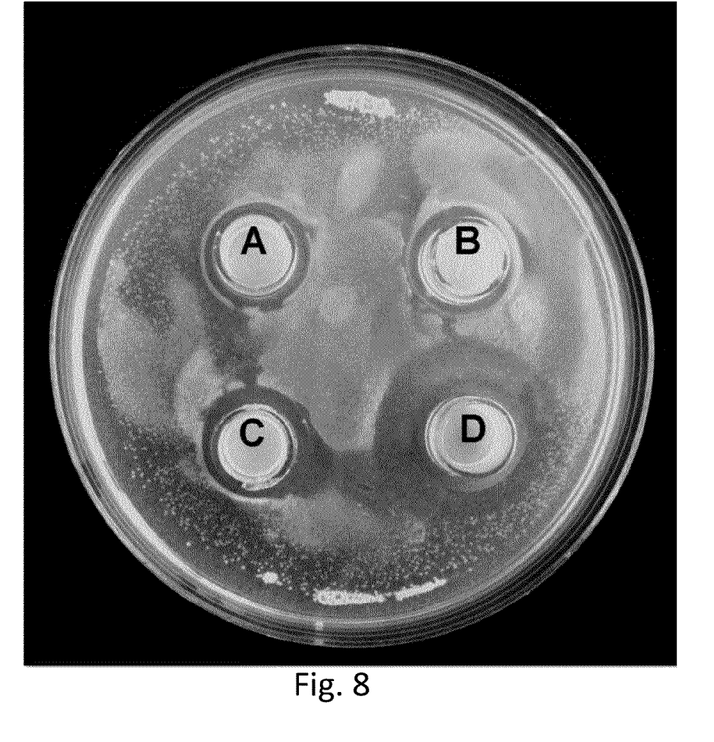
Figure 9:
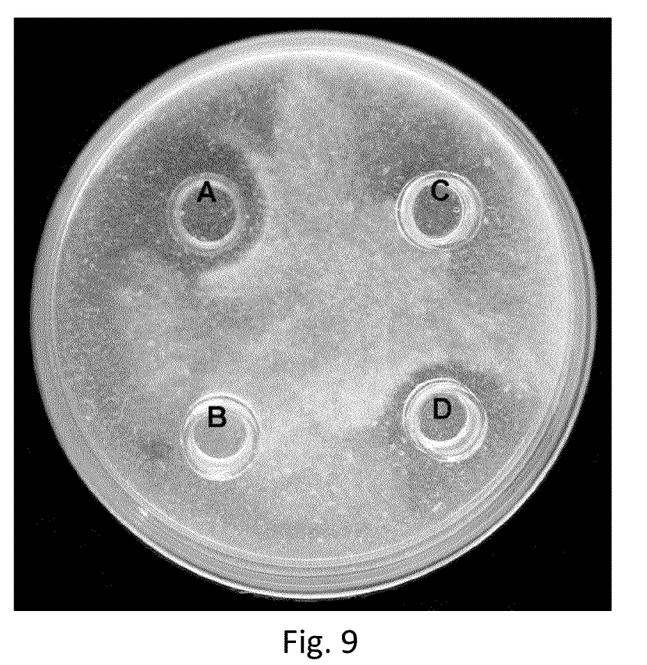
Figure 10:
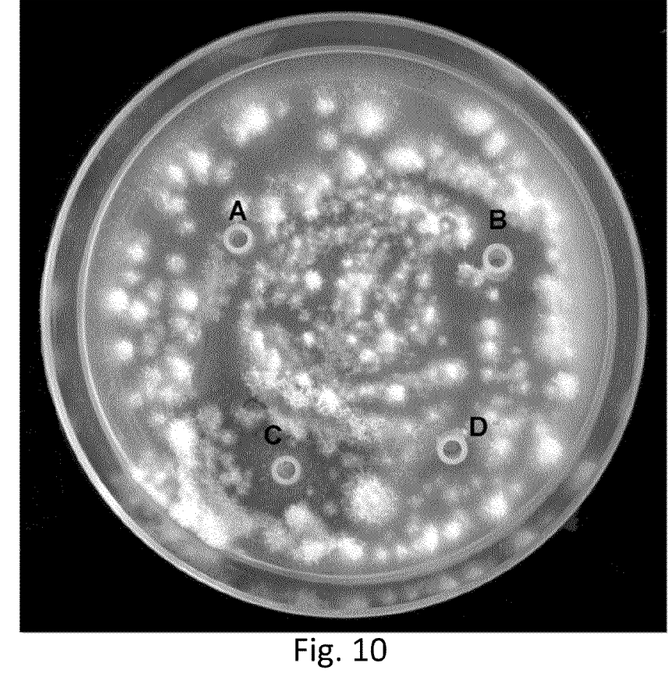

FIG. 6 shows that after 24 hrs of incubation with Ph-CA1 (10 ug/ml), cell membrane of most *C. albicans* cells (stained by FITC as green in the presence of propidium iodide) was damaged thus the propidium iodide entered into the cell to stain cells red.

Figure 11:
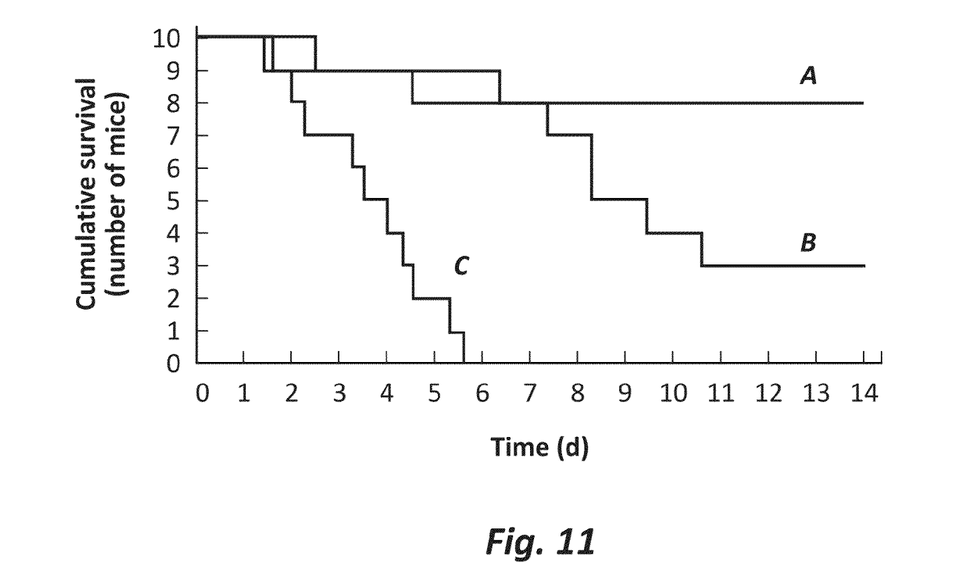

KungMing mice, half male and half female, weighing 18-22 g were injected intraperitoneally with 0.5 ml of *C. albicans* (ATCC 10231), $10^8$ CFU/ml. One hour after *C. albicans* injection, mice were injected intraperitoneally with 0.9% saline (A) alone as control (n=10) (C), or with amphotericin B (n=10, 1 ug/gm/day) (B), or with Ph-CA1 (n=10, 5 ug/gm/day) (A) daily for 14 days. The number of surviving animals was determined every 24 hours (FIG. 11).

Figure 12:
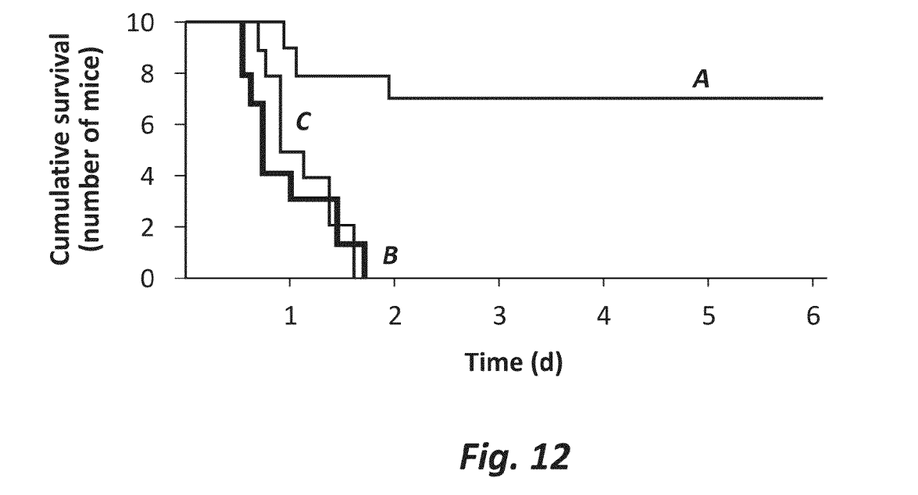

KungMing mice, half male and half female, weighing 18-22 g were injected intraperitoneally with 0.7 ml of *C. albicans* (ATCC 10231), $10^8$ CFU/ml. One hour after *C. albicans* injection, mice were injected in the tail vein with 0.9% saline alone as control (n=10) (C), or with amphotericin B (n=10, 1 ug/gm) (B), or with Ph-CA1 (n=10, 5 ug/gm) (A). The mice were then injected intraperitoneally with 0.9% saline alone, or with amphotericin B (n=10, 1 ug/gm), or with Ph-CA1 (n=10, 5 ug/gm) each day. The number of surviving animals was determined every 24 hours (FIG. 12). Considering the difference in molecular weight between Ph-CA1 (70 kDa) and amphotericin B (about 0.9 kDa), the in vivo antifungal activity of Ph-CA1 against systemic candidiasis was at least twenty times greater, on a molar basis, than that of amphotericin B.

Figure 13:
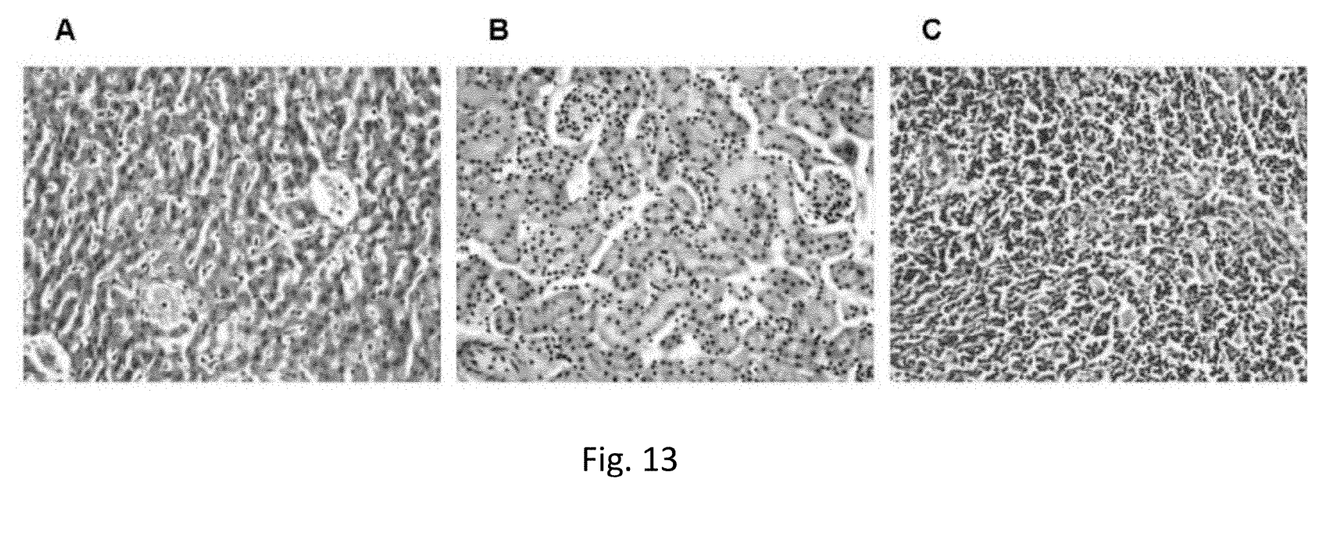

KungMing mice (n=10), half male and half female, weighing 18-22 g were injected intraperitoneally with Ph-CA1 (200 ug/mouse/day) for 20 days. The bodyweight of all mice was increased. There was no microscopic evidence of necrosis or inflammation in the livers, kidneys or spleens of mice (FIG. 13).

A 300 $m^2$ rice field (seed, gangyou 725) with *Magnaporthe grisea* infection was randomly divided as three zones. The middle 100 $m^2$ area was treated with water spraying twice as control, the left 100 $m^2$ area was treated with tricyclazole spraying twice (0.5 mg/ml and 1 mg/ml) and the right 100 $m^2$ area was treated with Ph-CA1 spraying twice (1 ug/ml and 2 ug/ml) at the tillering stage. The time interval between two sprayings was 7 days. Each 200 leaves were randomly examined in control and treatment areas to determine the protecting efficacy of Ph-CA1. The data are depicted below in Table I.

TABLE 1

| Examining date | Grades of impaired leaves | | | | | | Incident rate | Infected index | Protecting efficacy |
|---|---|---|---|---|---|---|---|---|---|
| | 0 | 1 | 3 | 5 | 7 | 9 | | | |
| One day Before Treatment | 152 | 27 | 14 | 6 | 1 | | 24 | 5.88 | |
| After Treatment | 89 | 57 | 30 | 7 | 7 | 8 | 55.5 | 17.38 | |
| Seven days Tricyclazole | 172 | 10 | 12 | 6 | | | 14 | 4.22 | 75.83 |
| Ph-CA1 | 67 | 12 | 13 | 8 | | | 16.5 | 5.05 | 70.94 |

Another 300 $m^2$ rice field (seed, gangyou 725) with *Magnaporthe grisea* infection was randomly divided as three zones. The middle 100 $m^2$ area was treated with water spraying once as control, the left 100 $m^2$ area was treated tricyclazole spraying once (1 mg/ml) and the right 100 $m^2$ area was treated with Ph-CA1 spraying once (2 ug/ml) at the head stage. About 200 ears were randomly examined in control and treatment areas to determine the protecting efficacy of Ph-CA1. The data are depicted below in Table II.

TABLE II

| | Grades of impaired ears | | | | | | Impaired ears rate | Infected index | Damage rate |
|---|---|---|---|---|---|---|---|---|---|
| | 0 | 1 | 3 | 5 | 7 | 9 | | | |
| Control | 178 | 33 | 22 | 11 | 2 | 2 | 28.6% | 8.33 | 4.2% |
| Tricyclazole | 184 | 16 | 9 | 2 | 2 | 0 | 13.62% | 3.5 | 1.63% |
| Ph-CA1 | 218 | 19 | 5 | 0 | 0 | 0 | 9.92% | 1.56 | 0.53% |

In both of the above in vivo protecting assays, the concentration of Ph-CA1 used was approximately 500 times smaller than that of tricyclazole. On a molar basis, the protecting effects of Ph-CA1 were three hundred times greater than that of tricyclazole. With these two factors taken together, the total effects of Ph-CA1 against rice blast disease was approximately $10^4$ to $10^5$ times greater than that of tricyclazole.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

The invention claimed is:

1. A method for preparing an antifungal polypeptide which inhibits growth of a fungus, wherein the method comprises:

(i) preparing a nucleic acid molecule by:

inserting a nucleic acid sequence encoding a fungal pheromone targeting agent into a selected position of the nucleic acid molecule; and inserting a nucleic acid sequence encoding a channel-forming domain of colicin Ia into the nucleic acid molecule so as to produce a fusion polynucleotide having a nucleic acid sequence encoding the antifungal polypeptide having the fungal pheromone targeting agent linked to the channel-forming domain, wherein the channel-forming domain comprises the amino acid sequence of SEQ ID NO: 8;

(ii) transfecting the fusion polynucleotide into a host cell; and (iii) allowing said host cell to produce said antifungal polypeptide.

2. The method of claim 1, wherein the fungal pheromone targeting agent is *Candida albicans* alpha-mating pheromone.

3. The method of claim 1, wherein said fungal pheromone targeting agent is from a pathogenic fungus selected from the group consisting of *Candidas, Aspergillus, Magnaporthes* and *Fusarium*.

4. The method of claim 3, wherein said *Candidas, Aspergillus, Magnaporthes* and *Fusarium* are selected from the group consisting of *Candida albicans, Candida tropicalis, Candida parapsilosis, Candida krusei, Candida dubliniensis, Aspergillus fumigatus, Aspergillus flavus, Aspergillus niger, Magnaporthe grisea* and *Fusarium moniliforme*.

5. The method of claim 1, wherein the colicin Ia is linked to the C-terminus of the fungal pheromone targeting agent.

6. The method of claim 1, wherein the channel-forming domain of colicin Ia is linked to the N-terminus of the fungal pheromone targeting agent.

7. The method of claim 1, wherein said antifungal polypeptide has a molecular weight of about 26,000 to about 70,000 daltons.

8. A method for preparing an antifungal polypeptide which inhibits growth of a fungus, wherein the method comprises:

(i) preparing a nucleic acid molecule by:

inserting a nucleic acid sequence encoding a *Candida albicans* alpha-mating pheromone into a selected position of the nucleic acid molecule; and inserting a nucleic acid sequence encoding a channel-forming domain of colicin Ia into the nucleic acid molecule so as to produce a fusion polynucleotide having a nucleic acid sequence encoding the antifungal polypeptide having the alpha-mating pheromone linked to the channel-forming domain, wherein the channel-forming domain comprises the amino acid sequence of SEQ ID NO: 8;

(ii) transfecting the fusion polynucleotide into a host cell; and (iii) allowing said host cell to produce said antifungal polypeptide.

9. The method of claim 8, wherein said *Candida albicans* alpha-mating pheromone comprises the amino acid sequence of SEQ ID NO: 3.

10. The method of claim 8, wherein said antifungal polypeptide comprises the amino acid sequence of SEQ ID NO: 5.

11. The method of claim 8, wherein the nucleic acid molecule comprises the nucleic acid sequence of SEQ ID NO: 2.

12. The method of claim 8, wherein the nucleic acid molecule comprises the nucleic acid sequence of SEQ ID NO: 4.

13. The method of claim 8, further comprising preparing a vector to have the nucleic acid.

14. A method for preparing an antifungal polypeptide which inhibits growth of a fungus, wherein the method comprises:

(i) providing a nucleic acid molecule having:

a nucleic acid sequence encoding a *Candida albicans* alpha-mating pheromone at a selected position of the nucleic acid molecule; and a nucleic acid sequence encoding a channel-forming domain of colicin Ia such that the nucleic acid molecule is a fusion polynucleotide having a nucleic acid sequence encoding the antifungal polypeptide having the alpha-mating pheromone linked to the channel-forming domain, wherein the channel-forming domain comprises the amino acid sequence of SEQ ID NO: 8;

(ii) transfecting the fusion polynucleotide into a host cell; and (iii) allowing said host cell to produce said antifungal polypeptide.

15. The method of claim 14, wherein said *Candida albicans* alpha-mating pheromone comprises the amino acid sequence of SEQ ID NO: 3.

16. The method of claim 14, wherein said antifungal polypeptide comprises the amino acid sequence of SEQ ID NO: 5.

17. The method of claim 14, wherein the nucleic acid molecule comprises the nucleic acid sequence of SEQ ID NO: 2.

18. The method of claim 14, wherein the nucleic acid molecule comprises the nucleic acid sequence of SEQ ID NO: 4.

19. The method of claim 14, further comprising preparing a vector to have the nucleic acid.

* * * * *

UNITED STATES PATENT AND TRADEMARK OFFICE
CERTIFICATE OF CORRECTION

| | | |
|---|---|---|
| PATENT NO. | : 8,663,916 B2 | Page 1 of 1 |
| APPLICATION NO. | : 13/048776 | |
| DATED | : March 4, 2014 | |
| INVENTOR(S) | : Qiu | |

It is certified that error appears in the above-identified patent and that said Letters Patent is hereby corrected as shown below:

On the Title Page, in Column 1, below Item (62), insert Item -- (30) Foreign Application Priority Data
Jan. 21, 2005  (CN).............. 200510020219.9 --.

Signed and Sealed this
Second Day of September, 2014

Michelle K. Lee
*Deputy Director of the United States Patent and Trademark Office*